United States Patent [19]

Schoon

[11] Patent Number: 5,219,645

[45] Date of Patent: Jun. 15, 1993

[54] ARTIFICIAL FINGERNAIL AND TOENAIL SURFACES COMPRISING AN CYANOACRYLATE HOMOPOLYMER IMPREGNATED FABRIC MATRIX

[75] Inventor: Douglas D. Schoon, Newport Beach, Calif.

[73] Assignee: Creative Nail Design, Carlsbad, Calif.

[21] Appl. No.: 827,890

[22] Filed: Jan. 30, 1992

Related U.S. Application Data

[63] Continuation of Ser. No. 486,545, Feb. 28, 1990, abandoned.

[51] Int. Cl.$^5$ .................. A45D 29/00; A61K 7/04; A61K 7/06; B32B 7/00

[52] U.S. Cl. .................. 428/261; 132/73; 424/61; 424/70; 428/245; 428/272; 428/273; 428/288; 428/292; 428/424.4; 428/542.2; 428/542.6; 428/913.3

[58] Field of Search .................. 132/73; 424/61, 70; 428/245, 288, 261, 272, 273, 288, 292, 424.4, 542.2, 542.6, 913.3

[56] References Cited

U.S. PATENT DOCUMENTS

| | | | |
|---|---|---|---|
| 3,216,983 | 11/1965 | Shelanski et al. | 260/88.3 |
| 3,478,756 | 11/1969 | Sautter et al. | 132/73 |
| 3,483,289 | 12/1969 | Michaelson et al. | 424/61 |
| 3,711,576 | 1/1973 | Hwa | 525/213 |
| 4,058,442 | 11/1977 | Lee et al. | 204/159.12 |
| 4,126,144 | 11/1978 | Duarte | 132/73 |
| 4,229,431 | 10/1980 | Lee, Jr. et al. | 424/61 |
| 4,260,701 | 4/1981 | Lee | 525/303 |
| 4,450,848 | 5/1984 | Ferrigno | 132/73 |
| 4,587,321 | 5/1986 | Sebag et al. | 528/27 |
| 4,590,069 | 5/1986 | Deckner et al. | 424/70 |
| 4,596,260 | 6/1986 | Giuliano | 132/73 |
| 4,626,428 | 12/1986 | Waisberg et al. | 424/61 |
| 4,646,765 | 3/1987 | Cooper et al. | 424/61 |
| 4,682,612 | 7/1987 | Giuliano | 132/73 |
| 4,690,369 | 9/1987 | Giuliano | 249/55 |
| 4,724,177 | 2/1988 | Russo | 428/35 |
| 4,860,774 | 8/1989 | Becker | 132/73 |

FOREIGN PATENT DOCUMENTS

| | | |
|---|---|---|
| 2107186 | 4/1983 | United Kingdom . |
| 2113245 | 8/1983 | United Kingdom . |
| 2114580 | 8/1983 | United Kingdom . |

OTHER PUBLICATIONS

Coover, "Cyanoacrylate Adhesives", Ch. 31, pp. 409-414 in Skeist ed. *Handbook of Adhesives* (1962).

Haidue et al *Basic Organometallic Chemistry*, Section 8.3, pp. 153-173 (1985).

Millet, "Cyanoacrylate Adhesives", Ch. 6. pp. 249-307 in Hartshorn ed., Structural Adhesives: Chemistry and Technology (1986).

Parkins et al. *An Introduction to Organometallic Chemistry*, Section 8.1.7. pp. 182-185 (1986).

Seymour, *Engineering Polymer Sourcebook*, Ch. 8, pp. 131-142 (1990).

*Primary Examiner*—Jenna L. Davis
*Assistant Examiner*—James D. Withers
*Attorney, Agent, or Firm*—Brown, Martin Haller & McClain

[57] ABSTRACT

A method is disclosed for the formation of artificial nail surfaces, whether natural nail coatings or nail extenders, which comprises first impregnating a fabric matrix with a cyanoacrylate monomer, forming the impregnated fabric matrix into an artificial nail surface shape and thereafter contacting the impregnated matrix with an organotin compound to cause the monomer to become polymerized and solidify in contact with the matrix and in the formed nail shape. In a preferred embodiment, the organotin compound is mixed with one or more additives in a liquid and the liquid is dispensed onto the monomer surface with an eyedropper, although, if desired, the additives can be incorporated separately prior to the contact of the impregnated matrix with the organotin compound. Also disclosed is a polymerizable nail surface formation system comprising a fabric matrix impregnated with a cyanoacrylate monomer and an organotin compound, the impregnated matrix being formed into an artificial human nail surface shape, wherein upon contact of the monomer and the compound, the compound catalyzes the polymerization of the monomer to form a solidified body in the nail surface shape.

The polymerized material finds use as an artificial nail surface for application to natural fingernails or toenails to enhance the physical properties and appearance of the nails.

26 Claims, No Drawings

ARTIFICIAL FINGERNAIL AND TOENAIL SURFACES COMPRISING AN CYANOACRYLATE HOMOPOLYMER IMPREGNATED FABRIC MATRIX

This is a continuation of application Ser. No. 07/486,545, filed Feb. 28, 1990 is now abandoned.

BACKGROUND OF THE INVENTION

1. Field of the Invention

The invention herein relates to compositions and methods for the formation of artificial human fingernail and toenail surfaces. More particularly, it relates to the formation of such surfaces using catalytic polymerization of cyanoacrylate monomers.

2. Description of the Prior Art

Artificial fingernail and toenail compositions in the form of nail coatings and extenders are well known and have become a major product line in the appearance and beauty industry. The appearance of one's fingernails (and in many cases also toenails) has become of importance to many fashion conscious individuals. The commercial artificial nail compositions have been used both for the purpose of enhancing the appearance of nails and also, in many cases, for enhancement of the physical properties of the nails, including providing strengthening to fragile nail surfaces.

It has been desirable to use cyanoacrylate polymers as part of artificial nail compositions. However, such has heretofore not been feasible in most cases, because of the problems with polymerizing (curing) cyanoacrylate monomers in the nail formation system.

The cyanoacrylate polymers are well known, especially for their adhesive properties. Their chemistry, methods of formation, compositions and uses are detailed widely; see, for example, Millet, "Cyanoacrylate Adhesives," Ch. 6, pp. 249–307, in Hartshorn, ed., *Structural Adhesives: Chemistry and Technology* (1986); Seymour, *Engineering Polymer Sourcebook*, Ch. 8, pp. 131–142 (1989); and Coover, "Cyanoacrylate Adhesives," Ch. 31, pp. 409–414, in Skeist, ed., *Handbook of Adhesives* (1962).

When used in the form of thin films, some cyanoacrylate monomers polymerize very rapidly in the presence of moisture. For these polymers, the amount of moisture in surrounding air is sufficient to cause complete polymerization of a thin film of the cyanoacrylate monomer, thus leading to the wide use of such cyanoacrylates as adhesives for bonding of tightly fitting surfaces.

However, many of these polymers, when in the form of thin films, lack flexibility, color stability or film strength. Other cyanoacrylate monomers polymerize only slowly in the presence of ambient moisture. In addition, many cyanoacrylate monomers (including those that otherwise would polymerize rapidly in the presence of ambient moisture) are initially mixed with inhibitors intended to prolong shelf life, which has the detrimental side effect that desirable polymerization speed is substantially slowed. There is thus a need for a catalyst that would speed the thin film polymerization of the normally slow cyanoacrylate monomers, overcome the retarding effects of inhibitors mixed with other cyanoacrylate monomers, and provide flexibility, color stability and/or strength to thin cyanoacrylate polymer films.

Moreover, in most nail formation systems, at least a portion of the cyanoacrylate monomer is present as a thicker layer (i.e., in "bulk"), and in such systems most cyanoacrylate monomers do not polymerize well. Polymerization in bulk is usually incomplete and the presence of unreacted monomer is detrimental to the properties of the polymerized product. It is believed that the polymerization of the bulk material is incomplete because the ambient moisture which catalyzes the thin film polymerization cannot penetrate satisfactorily into the body of the thicker layers of the cyanoacrylate monomer, and even that amount of moisture which does penetrate does not act effectively as a catalyst.

To this end there have been suggestions of a number of additive materials which could be incorporated into the cyanoacrylate monomer composition in an attempt to catalyze bulk polymerization fully. Some of the additives have been in the form of polymerization initiators but these are not usually satisfactory since they do not provide for shelf life prior to use. Another group of additives which has been suggested are promoters, which rely on separate initiation of polymerization by a third component. While such promoters can be blended with the cyanoacrylate monomers without causing any reaction, there is still the necessity of having a separate initiator before the polymerization promoters become effective.

While a number of the additives have been effective for completing or accelerating polymerization, they present problems, particularly in the area of safety, which can prevent their full utilization. As a first example of such problems, many of the catalytic reactions which result generate severe exotherms, which cause the polymerized cyanoacrylate material to become overheated. The presence of such excess heat can deteriorate the polymer bonds, discolor the polymerized body and detrimentally affect other additive materials which may be present in the composition or the surfaces with which the cyanoacrylate polymer is in contact. Thus, when cyanoacrylate polymers are used as a artificial nail compositions, the exothermic reaction which occurs can not only discolor the decorative nail surface but can often be of sufficient magnitude that the person's real nails and in some cases even the underlying tissue are seriously harmed by the heat. Of course even where there is no actual burning or blistering of the nails or tissue, the person usually experiences a great deal of discomfort from the heat.

It has also been found that many of the catalyst compositions are toxic, either when inhaled as fumes or when placed in contact with the human skin. Again considering nail compositions, a volatile toxic catalyst can be inhaled by both the wearer of the nail compositions and by the beautician or other person who applies the compositions. Both also can absorb the material through the skin, either by directly touching the composition while it is being applied to the wearer's nails or by absorption of fumes through the various skin surfaces which are in contact with the ambient air.

This is particularly significant when, as is commonly done, the compositions are sprayed onto the wearer's nails from a spray applicator held by the beautician at a distance of 6–12 inches (15–30 cm) from the nails. The spray creates a "mist cloud" which contacts the wearer's skin and the beautician's skin and is inhaled by both.

Finally, many of the proposed catalytic materials react only fairly slowly and do not provide quick polymerization of the slow or bulk cyanoacrylate monomers. This requires that such compositions must be set in place for some time before the cyanoacrylate monomer is fully polymerized. In many cases this is difficult or disadvantageous.

It would, therefore, be of great value to have a method and catalytic system which would allow for complete and rapid polymerization of cyanoacrylate monomers in the formation of artificial nail surfaces, so that the polymerization would be complete throughout the entire nail composition. Most importantly, such a method and system should also be safe for both the beautician to apply and the wearer to wear. Thus it would operate without the presence of any significant exotherm; would not cause harm to any adjoining material, whether human tissue or nails; would be satisfactory for use in either direct or indirect contact with people, of sufficiently low toxicity to be suitable for prolonged use by and in the presence of people and be acceptable for such human contact and use under the appropriate public health and cosmetics laws. Finally, it would not tend to discolor or distort the polymerized body; and the catalyst itself should be readily available,

SUMMARY OF THE INVENTION

In its broadest aspect, the invention herein is a method for the formation of artificial nail surfaces, whether natural nail coatings or nail extenders, which comprises first impregnating a fabric matrix with a cyanoacrylate monomer, forming the impregnated fabric matrix into an artificial nail surface shape and thereafter contacting the impregnated matrix with an organotin compound to cause the monomer to become polymerized and solidify in contact with the matrix and in the formed nail shape.

In a preferred embodiment, the contacting step comprises dispensing a catalyzing liquid comprising the organotin compound from an eyedropper onto the surface of the matrix or applying the catalytic liquid to the surface using a brush.

Another embodiment of the invention includes incorporating at least one additive intended to provide a desirable property to said artificial nail surface into the system with the organotin compound or separately in a step intermediate between the impregnation step and the application of the catalyst.

In another aspect, the invention is a polymerizable nail surface formation system comprising a fabric matrix impregnated with a cyanoacrylate monomer and an organotin compound, the impregnated matrix being formed into an artificial human nail surface shape, wherein upon contact of the monomer and the compound, the compound catalyzes the polymerization of the monomer to form a solidified body in the nail surface shape. The system may also contain various additives intended to provide beneficial properties to the artificial nail surface.

DETAILED DESCRIPTION AND PREFERRED EMBODIMENTS

The crux of the present invention lies in the discovery that cyanoacrylate monomers can be rapidly and safely catalyzed by organotin compounds, such that the resulting cyanoacrylate polymers can serve in combination with fabric matrices to form exceptional artificial nail surfaces, whether as nail coatings or nail extenders. The organotin compounds provide a unique class of cyanoacrylate monomer catalysts which serve to fully polymerize the monomer very rapidly and without any significant exotherm, and which have a significantly lower degree of toxicity than any of the currently used bulk catalysts. (The catalytic system itself is newly discovered along with the present invention, and is the subject of a copending patent application.)

As noted above, commercial artificial nail compositions have been used both for the purpose of enhancing the appearance of nails and also, in many cases, for enhancement of the physical properties of the nails, including providing strengthening to fragile nail surfaces. The normal methods of shaping and coloring of artificial nails can be used with this invention but the prior art application techniques are modified as will be described to take advantage of the unique catalyzing properties of the organotin compounds with the cyanoacrylate monomers.

An important element of the present invention is the development of a unique method of application of the composition, which method allows the formation of the unique nail surfaces in a manner not possible using the prior art techniques. In a typical application under the present system, one first impregnates a fabric matrix with a quantity of cyanoacrylate monomer. The impregnated fabric is applied to the wearer's natural nail surface, and a short interval (commonly about 30-60 seconds) is normally allowed to elapse to allow the surface of the monomer layer to become stabilized by surface polymerization. Thereafter, the organotin compound is preferably applied by dispensing the compound onto the surface of the cyanoacrylate layer, preferably by use of an eyedropper. This method permits close control of the catalysis and also provides a means by which in situ addition of additives can be accomplished. In many cases certain additives have been recognized by the prior art as potentially beneficial, but it has not been possible to blend them into the monomer prior to application to the nails. With this present method, however, such additives can be readily incorporated into the composition, since the can be added in the liquid dispensed from the eyedropper after the application of the monomer.

The monomer may be a liquid itself or may be dissolved in a solvent from which it is deposited by evaporation or concentration of the solvent. The quantity of monomer present as the impregnant will be sufficient to give form and shape to the artificial nail surface, whether as a nail extender or as a nail coating. Normally the quantity will be sufficient that the fabric matrix is completely filled with the monomer and the monomer covers both surfaces of the fabric matrix. Those skilled in the art will be readily able to determine a suitable quantity of monomer for each application, since the quantities will be essentially similar to the quantities of other fabric matrix impregnating liquids in current use in the formation of artificial nail surfaces. The organotin compound is normally dispersed in a solvent in which the compound is soluble but which does not dissolve the cyanoacrylate surface coating. The solvent should be one such as acetone which vaporizes very quickly leaving the organotin compounds to be dispersed through the cyanoacrylate layer to rapidly initiate and complete the bulk polymerization of the layer. Preferred as solvents are 1,1,1-trichloroethane, acetone, blends of acetone and 1,1,1-trichloroethane, ethyl acetate, blends of acetone and ethyl acetate, other chlorinated solvents or hydrocarbon solvents.

Any suitable fabric may be used as the fabric matrix. At the present time fiberglass is used to form the majority of the nail fabric, with silk and linen as commonly used. The nature of the fabric is not critical to the present invention, and it is contemplated that these materials, as well as any fabrics which come into use in the nail industry in the future, may be used in this invention.

The amount of cyanoacrylate monomer so used as an impregnant normally forms a layer sufficiently thick that the layer prevents the monomer from polymerizing as would a "thin layer" which can be catalyzed simply by the moisture in the ambient air. No particular quantitative thickness of the applied layer can be specified as denoting the boundary between a "thin film" and a "bulk layer," but the functional difference will be well known to those skilled in the art as exemplified by the discussion in the Millet reference at pages 259–260. It will suffice for the purposes of this invention to note that the typical cyanoacrylate monomer layer applied to human nails by either the wearer or by another individual such as a beautician will be sufficiently thick to clearly have bulk polymerization properties.

However, such bulk layers are not the only form of nail coating applicable to this invention. It is also contemplated that there will be instances where one wishes to add thin coating layers to an already existing artificial nail surface which already contains the fabric matrix. The present invention can be used to add a thin layer of cyanoacrylate monomer and then catalytically polymerize it with the organotin compound. Such will, as noted, make usable the "slow" or inhibited monomers and impart strength, flexibility and/or color stability to those monomers which otherwise catalyze in the presence of the ambient moisture. This provides beneficial results to the wearer that would otherwise not be present if the coating were to "self-cure" in the ambient air.

As an alternative to the eyedropper method, one may use a brush-on system, This can be advantageously used to physically blend the catalyst solution into the stabilized coating. In addition, a higher viscosity cyanoacrylate monomer can be used and some of or all of the organotin compound can be incorporated directly into the high viscosity monomer body.

It is also possible, and in some cases preferred, to use a combination of the two techniques, such that some of the cyanoacrylate monomer can be brushed on with of the beneficial additives but no organotin compound present and then the organotin compound applied by the dropper method. The dropper method provides benefits such as preventing the pitting of the polymer surface and avoiding any mist of catalyst material in the ambient air which would result from the prior art "spray-on" systems. It also eliminates the chance of cross contamination of the system. The brush-on method offers the benefits of fully blending the additives into the curing monomer and to some extent increasing the physical properties of the coating.

It will be recognized that a spray-on system can be used with this invention if desired. However, the spray-on techniques are known to cause numerous problems: they are difficult to control, they produce pits and dents in the fresh surfaces and the amount of catalyst being applied cannot be accurately determined. Consequently, such systems are not preferred.

The cyanoacrylate monomers which are polymerized by the organotin compounds of the present invention are any of the conventional cyanoacrylates which have been described in the art, particularly those described in the aforesaid Millet reference. These include the methyl, ethyl, isopropyl, n-butyl, methoxy and allyl cyanoacrylates. Most commercial cyanoacrylates are the ethyl and methyl ester monomers, but the low odor methoxy monomers are expected to become increasingly popular. There are many commercial sources and the products are sold under a variety of individual trade names and trademarks; see the aforecited Millet reference.

The chemistry and structure of organotin compounds are described in Haiduc et al., *Basic Organometallic Chemistry*, § 8.3, pp. 153–173 (1985) and Parkins et al., *An Introduction to Organometallic Chemistry*, §8.1.7, pp. 182–185 (1986). Those organotin compounds most useful in this invention will be those which have the formula $R_4Sn$ (I), where each R is an alkyl radical or the formula $R_2R'_2Sn$ (II), where each R and R' is an alkyl radical, with each R alkyl being a different radical from each R' alkyl, and all R and R' alkyl radicals may be different from each other. Preferably the R and R' alkyls are each a $C_1$–$C_{18}$ alkyl, more preferably normal alkyls. In a preferred embodiment of compound II, the R alkyl is an n-$C_1$–$C_8$ alkyl and the R' alkyl is an n-$C_9$–$C_{18}$ alkyl. Typical examples of preferred organotin compounds are dibutyl dilauryl tin (also known as dibutyl tin dilaurate) and tetraoctyl tin.

The amount of organotin compound required to catalyze cyanoacrylate monomer will typically be in the range of 1.0–3.0 parts (by weight), preferably 0.5–1.5, more preferably about 1.0 parts, of the compound per 100 parts of the cyanoacrylate monomer, although it is possible that higher or lower concentrations may be useful with some monomers. As an example, when considering the normal amount of coating placed on a human fingernail I have found that 1–2 drops of a solution of 0.5–1.0 grams of organotin compound dissolved in 100 ml of a blended acetone/1,1,1-trichloroethane solvent, as dispensed by a conventional hand held eyedropper, is quite satisfactory for complete polymerization (curing) of an artificial nail composition. The complete nail composition polymerizes thoroughly within about 1–5 seconds and it can thereafter be filed and/or have coatings such as nail polish applied.

It is possible to incorporate a variety of different kinds of additives into either or all of the original cyanoacrylate monomer layers prior to polymerization or into the solution containing the organotin compound. These include materials such as acrylic polymers to increase strength, flexibility, or moisture resistance, plasticizers to increase flexibility and impart crack arresting properties, ultraviolet radiation absorbers to inhibit yellowing from ultraviolet exposure; materials such as organofunctional silanes to modify the surface toward hydrophobicity and colorants to impart different hues to the polymer body. The particular types of materials and representative examples of each of the materials, as will as the individual amounts of each material to be present can be readily determined by those skilled in the art without any undue experimentation. It will be evident, of course, that any particular material, whether incorporated into the cyanoacrylate monomer layer or into the organotin solution, must not be such as to significantly impair the catalyzing properties of the organotin compound or to inhibit the cyanoacrylate monomer against polymerization catalyzed by the organotin compound.

The additives may be incorporated by being included in the catalytic liquid which contains the organotin compound, or, alternatively, the additive or additives may be included in a separate liquid system which contains no organotin compound. This separate liquid system would be placed on the initial cyanoacrylate layer and preferably worked into that layer, as with a brush. The combined materials would then be formed into the desired nail shape and thereafter the liquid containing the organotin compound would be applied to the formed body to catalyze the polymerization of the cyanoacrylate monomer.

A wide variety of beneficial properties and results have been observed by use of the present invention to catalyze the cyanoacrylate monomers. These include, but are not limited to, the absence of any violent uncontrolled exotherm upon polymerization; the absence of any degree of exotherm which would impart damage to the human nail surfaces or the underlying tissue; lower shrinkage of the polymerized cyanoacrylate layer than is observed with moisture catalyzed systems or systems catalyzed with conventional prior art catalysts; lower stresses on the coating or adhesive bond, as a direct result of the lower shrinkage of the polymerized body; markedly lower degree of potential toxicity as compared to use of conventional prior art catalysts; lack of any significant absorption of the catalyst through the skin; long-term stability of the organotin compound in solution in the solvent; and imparting of flexibility, color stability and enhanced strength to the nail composition layers.

It will be evident from the above that there are many embodiments of this invention which those skilled in the art will recognize to be clearly within the scope and spirit of the invention even though not expressly stated above. The above description is therefore intended to be exemplary only and the full scope of the invention is to be defined solely by the appended claims.

I claim:

1. An artificial nail structure comprising a fabric matrix impregnated with a cyanoacrylate homopolymer and formed into an artificial human nail surface shape, said cyanoacrylate homopolymer formed by the polymerization of a cyanoacrylate monomers upon contact with a catalystic organotin compound.

2. A structure as in claim 1 wherein said organotin compound has the formula $R_4Sn$, where each R is an alkyl.

3. A structure as in claim 2 wherein each said alkyl is a $C_1$–$C_{18}$ alkyl.

4. A structure as in claim 3 wherein each said alkyl is a normal alkyl.

5. A structure as n claim 4 wherein said alkyl is n-octyl.

6. A structure as in claim 1 wherein said organotin compound has the formula $R_2R'_2Sn$, where each R and R' is an alkyl, with each R alkyl being a different species from each R' alkyl.

7. A structure as in claim 6 wherein each said alkyl is a $C_1$–$C_{18}$ alkyl.

8. A structure as in claim 7 wherein each alkyl is a normal alyl.

9. A structure as in claim 89 wherein each said R alkyl is an n-$C_1$–$C_8$ alkyl and each said R' alkyl is an n-$C_9$–$C_{18}$ alkyl.

10. A structure as in claim 9 wherein each said R alkyl is n-butyl and each said R' alkyl is n-lauryl.

11. A structure as in claim 1 wherein said cyanoacrylate monomer is the ethyl ester of 2-cyanoacrylic acid.

12. A structure as in claim 1 wherein said cyanoacrylate monomer is the methyl ester of 2-cyanoacrylic acid.

13. A structure as in claim 1 wherein said cyanoacrylate monomer is the methoxy ester of 2-cyanoacrylic acid.

14. A system as in claim 1 further comprising at least one additive selected from the group consisting of stabilizers, colorants, plasticizers, ultraviolet radiation absorbants and tougheners.

15. A structure as in claim 1 wherein said organotin compound is present in a concentration of 1.0–3.0 parts by weight per 100 parts of the cyanoacrylate monomer.

16. A structure as in claim 15 wherein said organotin compound is present in a concentration of 0.5–1.5 parts by weight per 100 parts of the cyanoacrylate monomer.

17. A structure as in claim 8 wherein said organotin compound is present in a concentration of about 1.0 parts by weight per 100 parts of the cyanoacrylate monomer.

18. An artificial nail surface formed by first impregnating a fabric matrix with a cyanoacrylate monomer, molding said impregnated fabric matrix into an artificial nail surface shape and thereafter contacting said impregnated matrix with an organotin compound to cause said monomer to homopolymerize and solidify to form said nail surface shape.

19. An artificial nail surface as in claim 18 wherein said contacting of said impregnated matrix comprising dispensing a catalyzing liquid comprising said organotin compound from an eyedropper onto the surface of said matrix or applying said catalytic liquid to said surface using a brush.

20. An artificial nail surface as in claim 19 wherein said catalyzing liquid comprises, in addition to said organotin compound, at least one additive.

21. An artificial nail surface as in claim 20 wherein said additive is selected from the group consisting of stabilizers, colorants, plasticizers, ultraviolet radiation absorbants and tougheners.

22. An artificial nail surface as in claim 21 wherein there is a plurality of said additives.

23. An artificial nail surface formed as in claim 18 including further comprising, following said impregnation, applying to said cyanoacrylate monomer impregnated fabric matrix a non-catalytic liquid system comprising at least one additive and thereafter contacting said impregnated matrix with said organotin compound.

24. An artificial nail surface as in claim 23 wherein said non-catalytic liquid system is physically worked into the impregnated fabric matrix and formed into the nail surface shape prior to said contact with said organotin compound.

25. An artificial nail surface as in claim 24 wherein said additive is selected from the group consisting of stabilizers, colorants, plasticizers, ultraviolet radiation absorbants and tougheners.

26. An artificial nail surface as in claim 25 wherein there is a plurality of said additives.

* * * * *